US006034059A

United States Patent [19]
Fryklund et al.

[11] Patent Number: 6,034,059
[45] Date of Patent: Mar. 7, 2000

[54] TREATMENT OF CATABOLIC STATES USING AUTHENTIC IGF-1 AND HYPOCALORIC AMOUNT OF NUTRIENTS

[75] Inventors: Linda Fryklund, Sollentuna, Sweden; Peter Gluckman, Auckland, New Zealand; Anna Skottner, Ekerö, Sweden

[73] Assignee: Chiron Corporation, Emeryville, Calif.

[21] Appl. No.: 07/979,863

[22] PCT Filed: Aug. 22, 1991

[86] PCT No.: PCT/SE91/00557

§ 371 Date: Mar. 17, 1993

§ 102(e) Date: Mar. 17, 1993

[87] PCT Pub. No.: WO92/03154

PCT Pub. Date: Mar. 5, 1992

[30] Foreign Application Priority Data

Aug. 24, 1990 [SE] Sweden .................................. 9002731

[51] Int. Cl.[7] ........................... A61K 38/00; A61K 38/18
[52] U.S. Cl. .................................. 514/12; 514/2; 514/21; 530/324; 530/303; 530/399; 435/69.1
[58] Field of Search .................................. 530/399, 324, 530/303; 514/2, 12, 21, 24; 435/69.1

[56] References Cited

FOREIGN PATENT DOCUMENTS

| 0 303 746 | 2/1989 | European Pat. Off. . |
| 218811 | 7/1991 | New Zealand . |
| WO 87/01038 | 2/1987 | WIPO . |
| WO 87/04074 | 7/1987 | WIPO . |
| WO 89/05822 | 6/1989 | WIPO . |
| WO89/05822 | 6/1989 | WIPO . |

OTHER PUBLICATIONS

Jacob et al., "Acute Effects of Insulin–Growth Factor 1 on Glucose and Amino Acid Metabolism in the Awake Fasted Rat", *Am. Soc. Clin. Invest.*, May 1989, vol. 83, pp. 1717–1723.

G. C. Liggins, Premature Delivery of Foetal Lambs Infused with Glucocorticoids, *J. Endocr.*, 1969, 515–523, 45 Great Britian.

G. C. Liggins et al., A Controlled Trial of Antepartum Glucocorticoid Treatment for Prevention of the Respiratory Distress Syndrome in Premature Infants, *Pediatrics*, Oct. 1972, 515–525, 50(4).

Collaborative Group on Neonatal Seroid Therapy, Effect of Antenatal Dexamethasone Administration on the Prevention of Respiratory Distress Syndrome, *Am. J. Obstet. Gynecol.*, Oct. 1, 1981, 276–286, 141(3), USA.

Don Schalch et al., The Effects of a Calorie–Restricted Diet on Growth Hormone, *Endocrinology*, 1985, 2307–2312, 117(6), USA, Abstract CA104 (3):15738M.

J. McK. Manson et al., Positive Nitrogen Balance with Human Growth Homrone and Hypocaloric Intravenous Feeding, *Surgery*, Aug. 1986, 188–197, 100(2), USA.

Naomi Hizuka et al., Insulin–Like Growth Factor I Stimulates Growth in Normal Growing Rats, *European J. Pharmacology*, 1986, 143–146, 125, Elsevier Science Publishers B.V.

Hans–Peter Guler et al., Short–Term Metabolic Effects of Recombinant Human Insulin–Like Growth Factor I in Healthy Adults, *The New England Journal of Medicine*, Jul. 16, 1987, 137–140, 317(3).

Takaharu Fujioka et al., Sustained–Release Pharmaceuticals containing hormones and polymeric carriers, Abstract: 106:72941n, *Chem. Abst.*, 385–386, 106.

W. E. Sonntag et al., Chronic Ethanol Feeding Inhibits Plasma Levels of Insulin–Like Growth Factor–1, *Life Sci*, 1988, 1325–1330, 43 (16), Abstract.

U. O'Sullivan et al., Insulin–Like Growth Factor–1 (IGF–1) in Mice Reduces Weight Loss During Starvation, *Endocrinology*, 1989, 2793–2794, 125(5), The Endocrine Society, USA.

Zhu–Ming Jiang et al., Low–Dose Growth Hormone and Hypocaloric Nutrition Attenuate the Protein–Catabolic Response After Major Operation, *Ann. Surg.*, Oct. 1989, 513–525, 210(4), USA.

Kazue Takano et al., Effects of sc Administration of Recombinant Human Insulin–Like Growth Factor I (IGF–I) on Normal Human Subjects, *Endocrinol. Japon.*, 1990, 309–317, 37(2).

R. G. Douglas et al., Metabolic Effects of Recombinant Human Growth Hormone: Isotopic Studies in the Postabsorptive State and During Total Parenteral Nutrition, *Br. J. Surg.*, Jul. 1990, 785–790, 77(7), Butterworth–Heinemann Ltd.

P.J. Pacy et al. Influence of Glucagon on Protein and Leucine Metabolism: A Study in Fasting Man with Induced Insulin Resistance, *Br. J. Surg.*, Jul. 1990, 791–794, 77(7), Butterworth–Heinemann Ltd.

Fritz F. Horber et al., Human Growth Hormone Prevents the Protein Catabolic Side Effects of Prednisone in Humans, *J: Clin. Invest.*, Jul. 1990, 265–272, 86.

Joel D. Kopple, Clinical Experience with Parenteral Nutrition in Acute Renal Failure, in *Nutritional Support in Organ Failure*, ed. T. Tanaka and A. Okada, 1990, 393–404, Elsevier Science Publishers (Biomedical Division).

Jan L. Walker et al., Effects of the Infusion of Insulin–Like Growth Factor I in a Child with Growth Hormone Insensitivity Syndrome (Laron Dwarfism), *The New England Journal of Medicine*, May 23, 1991, 1483–1488, 324(21).

Elias A. Lianos et al., Mesangial Cell Immune Injury, *J. Clin. Invest.*, Aug. 1991, 623–631, 88.

(List continued on next page.)

*Primary Examiner*—Frank C. Eisenschenk
*Attorney, Agent, or Firm*—W. Murray Spruill; Joseph H. Guth; Robert P. Blackburn

[57] ABSTRACT

IGF-1 and a hypocaloric amount of nutrient are used to treat a catabolic state in a patient. The IGF-1 and nutrient can be administered simultaneously, separately or sequentially. The amounts of IGF-1 and hypocaloric amount of nutrient are effective for the treatment of the catabolic state.

12 Claims, 6 Drawing Sheets

OTHER PUBLICATIONS

R. G. Douglas et al., The Effects of Infusion of Insulinlike Growth Factor (IGF) I, IGF–II, and Insulin on Glucose and Protein Metabolism in Fasted Lambs, *J. Clin. Invest.,* Aug. 1991, 614–622, 88.

Jacob et al., "Acute Effects of Insulin–like Growth Factor 1 on Glucose and Amino Acid Metabolism in the Awake Fasted Rat", *Am. Soc. Clin. Invest.,* May 1989, vol. 83, pp. 1717–1723.

Low–dose growth hormone and hypocaloric nutrition attenuate the protein–catabolic response after major operation, Dialog Information Services, File 155, Medline 66–91/May, Dialog Accession No. 07118481, Jiang ZM et al., Ann Surg Oct. 1989, 210 (4) pp. 513–524.

Koea, J. B. et al., "Synergistic Effect of Insulin–Like Growth Factor–I . . . in Fasted Lambs".

Schalch et al., The Chemical Abstracts, 104 (3): 15738 m.

O'Sullivan et al. The Chemical Abstracts. 112(9):70510w.

Kopple, Proceedings of the Int. Sym. ICS836, 393–404, 1990 Conference: Int. Sym., Osaka, Japan Nov. 21–23, 1988.

Sonntag Life Science, 43(16), 1325–1330, 1988 (abst.).

Fujioka et al., The Chemical Abstracts, 106, 72941n.

Ann. Sur. Oct. 1989, vol. 210(4), pp. 513–524 (Abstract).

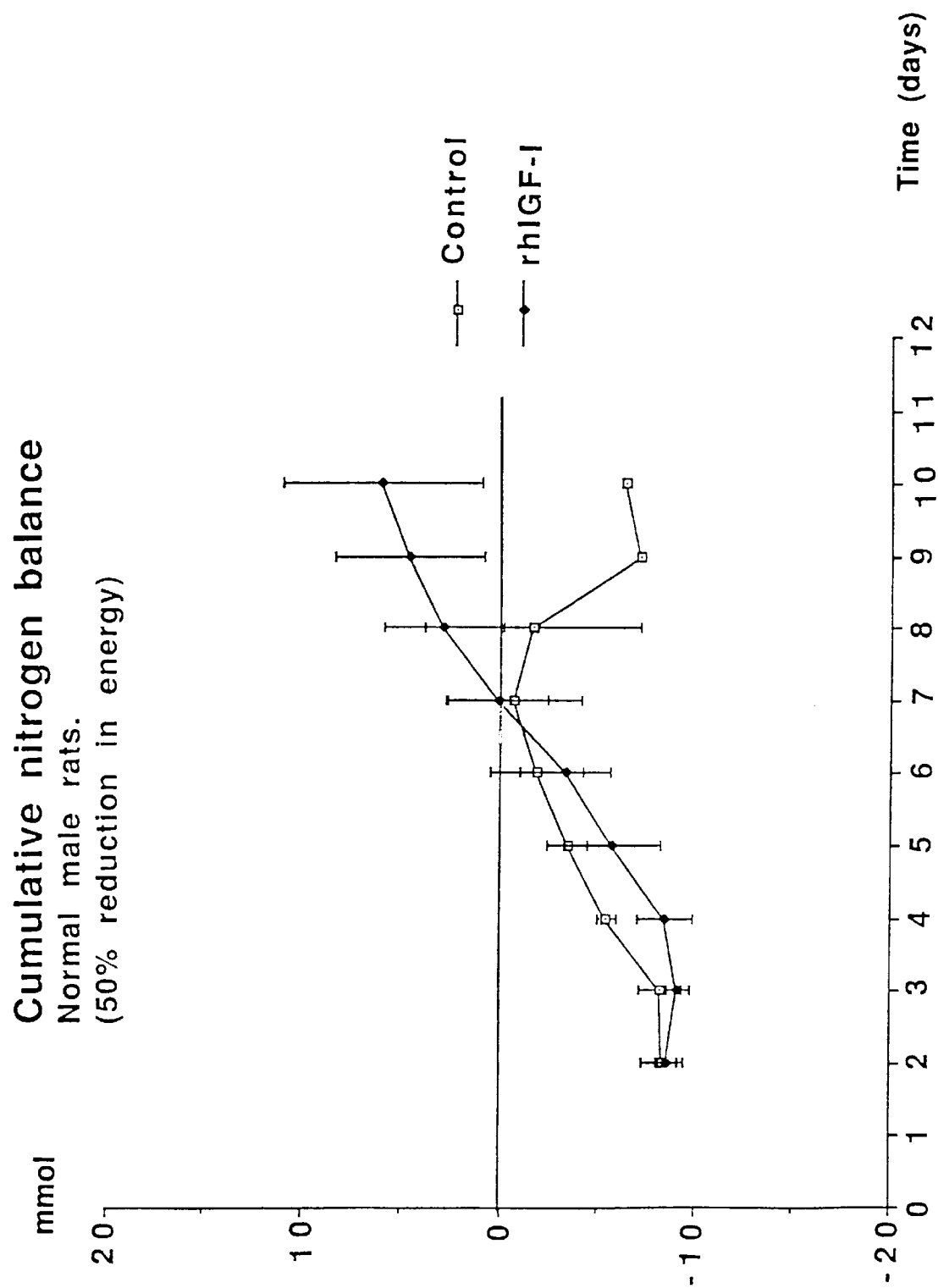

Percentage change of net protein loss during rhIGF-I infusion.

*, ** = significantly different from 180 min

TREATMENT OF CATABOLIC STATES USING AUTHENTIC IGF-1 AND HYPOCALORIC AMOUNT OF NUTRIENTS

DESCRIPTION

1. Technical Field

This invention relates to a method and a product for the treatment or prevention of the catabolic state in patients, involving the administration of insulin-like growth factor 1 (IGF-1).

2. Background Art

IGF-1 is a peptide belonging to the somatomedin family. It is comprised of 70 amino acids, including 3 disulphide bonds. Its amino acid sequence is known. IGF-1 is normally found in the circulation bound to at least two different classes of binding proteins (ca 150.000 D) and the low molecular weight binding protein (ca 30.000 D). IGF-1 is mitogenic in cell lines (i.e in vitro) and has been shown to stimulate growth in growth hormone (GH) deficient animals.

The IGF-1 concentration is in plasma (blood), at least partly, regulated by GH but also by other hormones, such as thyroxine, and by the nutritional status.

A wide variety of clinical conditions can lead to loss of weight and muscle in patients and in particular to protein depletion. Examples of possible causes are burns, multiple trauma, sepsis, major surgery and malignant tumours. In some cases, patients cannot be fed orally at all (e.g in the case of gastrointestinal surgery) or only at an inadequate caloric level. In other instances nutrients taken orally cannot be absorbed or cannot be absorbed with normal efficiency via the gastro-intestinal tract. In such cases intravenous feeding must be utilised but it is difficult or sometimes impossible to supply normal caloric requirements by the intravenous route. There is also a risk for liquid overload.

In such circumstances there is a need to be able to treat or prevent a catabolic state whilst supplying the patient with a diet that, to the extent that it is utilised by the body, is inadequate to meet his/her normal caloric requirements. Such a diet is referred to herein as a "hypocaloric diet".

It has been suggested (International Patent Application WO 87/04074) that protein accretion or nitrogen retention can be promoted in the case of a hypocaloric diet by the administration of growth hormone (GH). It is thought that any beneficial effect resulting from the administration of GH may be derived from an increased level of IGF-1 in the bloodstream that has been observed in some cases. On the other hand, there is conflicting evidence both from human and ovine studies where administration of GH did not bring about any IGF-1 response. In any event, not all classes of patients are able to respond to the administration of GH by an increase in IGF-1 levels. Indeed, relative GH resistance is frequently seen in catabolic states.

Moreover, very young children particularly those less than one year of age do not have the necessary GH receptors and in severely-starved adults the GH receptor function is impaired or the receptors are reduced in number so that administration of GH in such cases is ineffective or only effective in greatly increased (i.e pharmacological) quantities. High doses of GH are undesirable as they can lead to hyperglycaemia and in any event the drug is expensive. Futhermore, in the case of adults, it is not always easy to determine whether a given patient will be able to respond to the treatment with GH or not.

It has also been suggested that treatment with certain analogues of IGF-1 can lead to increased growth rates in animals (International Patent Application WO 87/01038, WO 89/05822). It was postulated that the use of analogues having certain amino acid residues absent from the N-terminus would reduce the degree of binding to the IGF-1 binding proteins. This was based on the assumption that only free (i.e unbound) IGF-1 has the desired anti-catabolic activity. On the other hand, it has been suggested that freely-circulating IGF-1 may be responsible for the known tendency of that material to cause undesirable hypoglycaemia. In fact, the prevailing opinion was that systemically administered IGF-1 could not be used therapeutically for that reason. However, we now believe that the bound forms of IGF-1 may be responsible for the desired anabolic effects.

SUMMARY OF INVENTION

We have found that the administration of authentic IGF-1, whether obtained by recombinant DNA or other techniques, in conjunction with a hypocaloric diet, is advantageous in the treatment of catabolic states.

Tests carried out by us on lambs which had been fasted for 48 hours and which were in negative nitrogen balance indicated that administration of IGF-1 could reduce protein catabolism at doses that did not affect carbohydrate metabolism (i.e which are not hypoglycaemic). These tests indicated a positive effect on protein metabolism within only 120 minutes of starting an IGF-1 infusion. Thus, a positive effect was noticed much more quickly then would have been expected. Our tests indicated that the effect of IGF-1 was both to reduce protein breakdown and to stimulate protein synthesis, both in liver and the skeletal muscle. This conclusion is supported by other work carried out by us on hypophysectomized rats. The rats were supplied by infusion with 200 micrograms of rhIGF-1 daily (equals 60 micrograms IGF/kg/hour) for 7 days. The rats showed an increase in body weight without a change in food intake, indicating increased food utilization, and also a lower rate of excretion of urea, which indicates that IGF-1 can suppress protein breakdown. Again, no undesirable hypoglycaemic effects were observed.

According to one aspect of this invention, a product for the treatment or prevention of a catabolic state in a patient comprises authentic IGF-1 and a hypocaloric amount of nutrient, for simultaneous, separate, or sequential use.

The invention also includes use of authentic IGF-1 and a hypocaloric amount of nutrient in the manufacture of a product for the treatment or prevention of a catabolic state in a patient.

The invention further includes a method for the treatment or prevention of a catabolic state by administering to a patient authentic IGF-1 in conjunction with a hypocaloric diet.

BRIEF DESCRIPTION OF THE FIGURES

FIG. 4 is a graph showing cumulative nitrogen balance.

PREFERRED AND VARIOUS MODES FOR CARRYING OUT INVENTION

Figure 1:
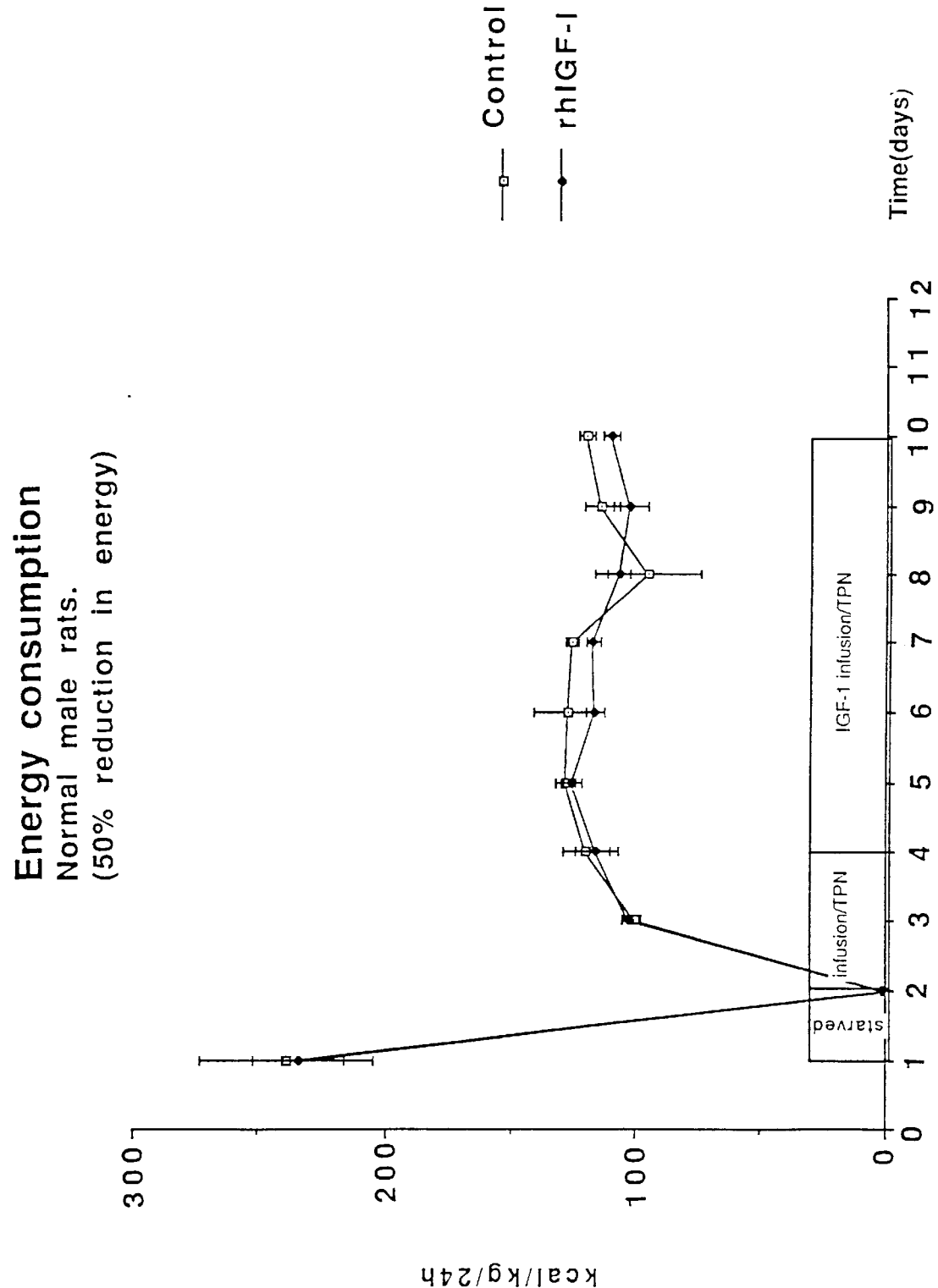
FIG. 1 is a graph showing energy consumption.
Figure 2:
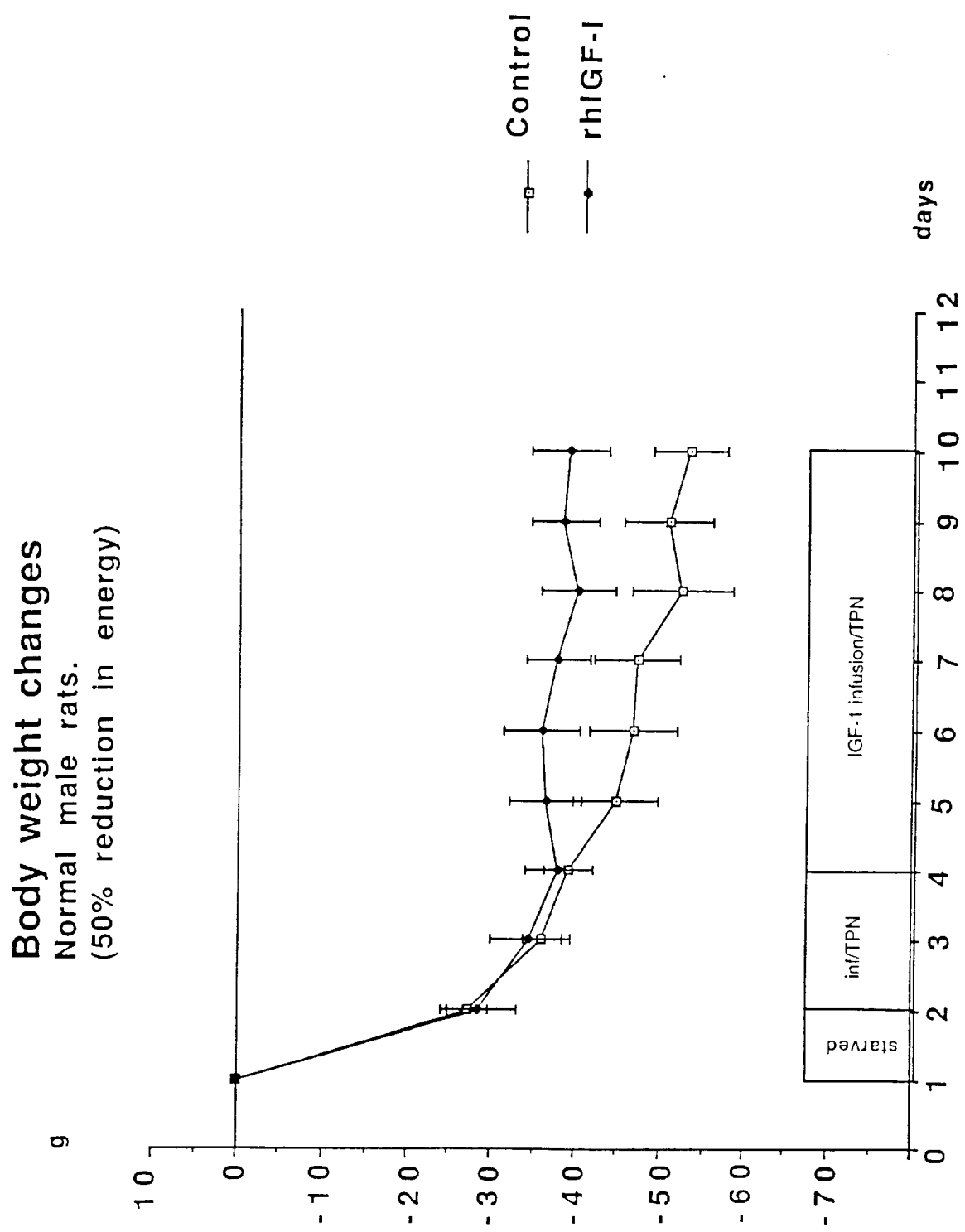
FIG. 2 is a graph showing body weight changes.

By "authentic IGF-1" we mean IGF-1 having the complete amino acid sequence of natural human IGF-1. It is preferably obtained by recombinant DNA technology, e.g from transformed yeast cells.

By "prevention of a catabolic state" we include an effect in which protein synthesis is stimulated and/or an effect in which the rate of protein degradation is decreased.

We have found that the response time (as evidenced by the onset of protein accretion) of a patient to treatment in accordance with the invention is much shorter then would have been expected from the results obtained from administration of GH in conjunction with a hypocaloric diet, even talking into account that it is known that administration of GH normally leads to an increase in the level of IGF-1. Also, a surprisingly low dose of authentic IGF-1 in conjunction with a hypocaloric diet has been found to be effective. It is advantageous to be able to administer relatively low doses of the drug in order to minimise the hypoglycaemic effect of IGF-1. Further, in the case of the critically ill patient the rapid response available by treatment with authentic IGF-1 may be essential for survival.

The nutrient may be for oral, intragastric or parenteral (especially intravenous) administration. The amount of nutrient supplied is preferably such that which is utilised by the patient provides up to 90%, and preferably up to 70%, of the resting metabolic requirement. This may, for example, be achieved by supplying to the patient up to about 60 kcal/kg of body weight per day for an adult.

The nutrient may include one or more carbohydrates (e.g. glucose) and/or lipids, and/or proteins or protein-amino acids that are found in proteins.

The dose of authentic IGF-1 is preferably 0.02 to 20 mg/kg/day, more preferably 0.05 to 2 mg/kg/day.

The IGF-1 may be for administration by intravenous infusion, possibly in combination with total parenteral nutrition (TPN). Alternatively, the IGF-1 may be for administration by other means, such as subcutaneous or intramuscular injection, orally, or nasally.

This invention has a wide range of potential applications.

In sick premature infants on parental nutrition positive nitrogen balance is difficult to achieve without fluid overload. Because of GH receptor immaturity GH will not be efficacious. Thus IGF-1 will prove useful in very low birth weight infants (e.g <27 weeks gestation) requiring nutritional support, in neonates following surgery (particularly bowel surgery) or sepsis and in patients with gastroenteritic disease (e.g necrotising enterocolitis).

In all prepubertal children GH receptor levels are relatively low. Therefore in such chidren who are severely ill and in negative nitrogen balance authentic IGF-1 in conjunction with hypercaloric diet will be therapeutically advantageous. Similarly in hypothyroid individuals, relative GH resistance is likely. In such patients and in hypopituitary adults or children not receiving GH where an emergency situation arises leading to catabolism (e.g trauma or sepsis) IGF-1 will be more effective than GH as it takes some days for GH to induce the GH-receptor and valuable therapy time will be lost. Individuals with genetic defects in the GH-receptor (e.g Laron dwarfs, pygmies, etc.) who for other reasons require metabolic support will respond specifically to IGF-1. As under-nutrition (either hypocaloric, low protein or mixed) can lead to GH resistance either due to a loss of high affinity GH-receptors or to postreceptor mechanisms leading to a failure to induce IGF-1 release, IGF-1 will be useful in situations such as chronic bowel disease, e.g Crohns disease, protein losing enteropathies, short gut syndromes, postgastroenteritic malabsorption states, cystic fibrosis, chronic or acute pancreatitis, and hepatitis. It will also be effective in other states where only a hypocaldric diet can be given which creates a disadvantageous clinical syndrome (anorexia nervosa, bulimia, vomiting in pregnancy, etc.) GH resistance is also reported in chronic renal failure and authentic IGF-1 may be more advantageous than GH in such situations particularly because the increased feed efficiency means that muscle sparing is possible at lower net protein intakes thus reducing the load on the kidneys in terms of urea excretion. As the liver is the major source of systemic IGF-1, acute or chronic liver disease will induce GH resistance. Thus authentic IGF-1 may be particularly valuable in acute hepatic failure where protein loading can be dangerous and in catabolic states associated with chronic liver disease.

As protein loss, particularly from skeletal muscle, is detrimental in acute situations such as post surgery (where it can postpone or prolong recovery), trauma, acute renal failure due to many causes (for the reasons explained above), the rapid anabolic and anticatabolic effects of authentic IGF-1 offer a unique approach to acute therapy. As IGF-1 therapy will reduce the amount of parental nutrition needed because of its effects on feed conversion, allowing a hypocaloric diet to be supplied, fluid requirements will be less so that in situations of catabolism for any reasons with coexistent heart failure, renal failure, or severe hypertension, authentic IGF-1 will be an important therapeutic aid.

The results on tests on rats and lambs are now given by way of non-limiting examples, and with reference to the drawings (FIGS. 1 to 6b).

EXAMPLE 1

A nutrient mixture was made up from the following components:
(1) 16.88 ml of a 50% glucose solution
(2) 4.05 ml of a 20% "Intralipid" solution
(3) 8.34 ml of 20% "Vamin 18" solution
"Intralipid" and "Vamin" are registered trade marks. "Intralipid" is a fat emulsion and "Vamin 18" is an amino acid mixture.

Rats were supplied with a hypocaloric amount of the above nutrient mixture at a daily rate of 20–25 ml by intravenous infusion, simultaneously with a daily dose of 1 mg (equals ca 190 micrograms/kg/hour) of recombinant authentic human IGF-1. This provided a caloric intake of 95–125 kcal/kg/day. A control group of rats was infused with normal saline solution instead of the IGF-1. The effect on the rats is set out in the form of graphs in FIGS. 1 to 4.

Figure 3:
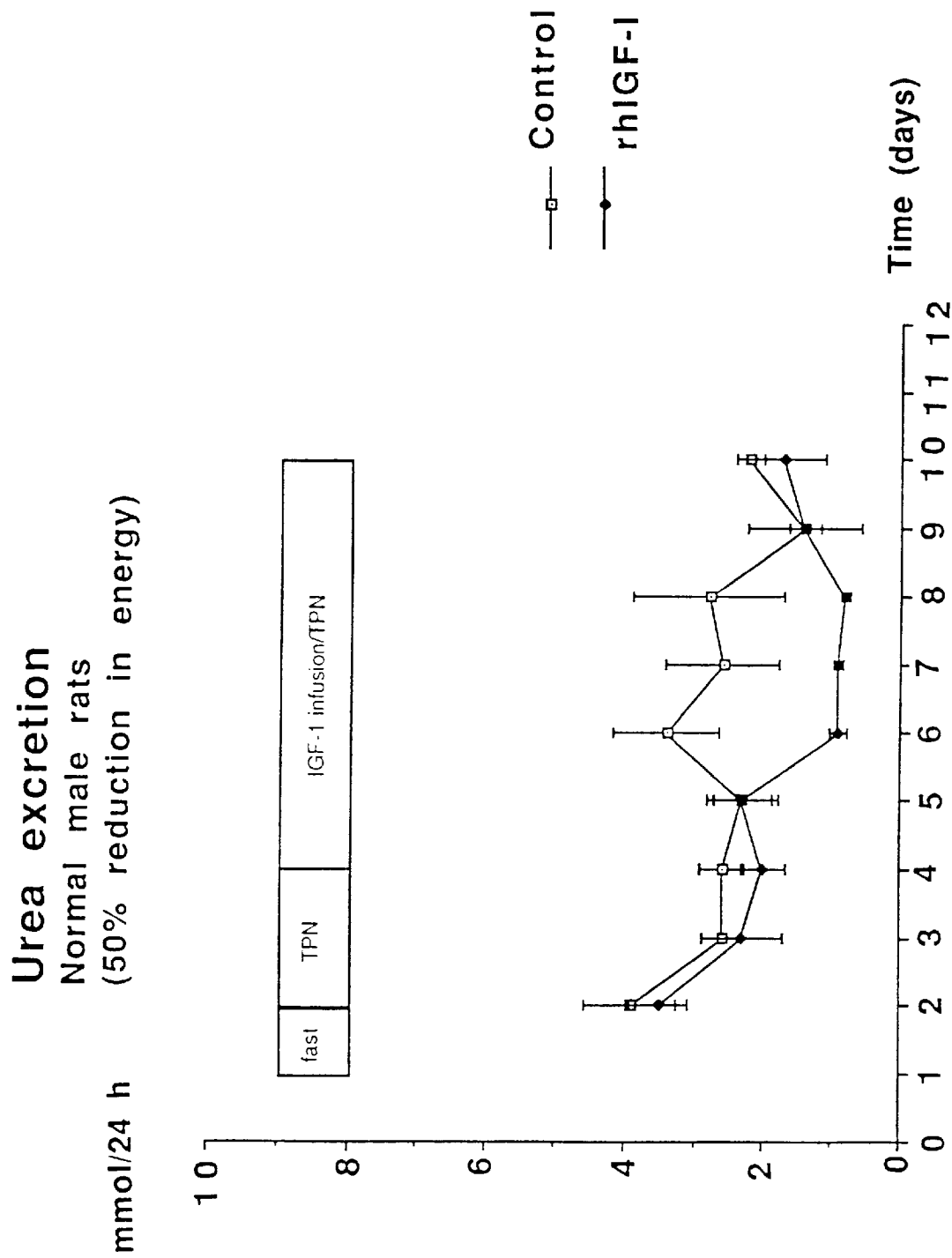
FIG. 3 is a graph showing urea excretion.

The figures show that the rats were fasted for 1 day, were then supplied with TPN alone for 2 days, and then TPN together with the IGF-1 for a futher 6 days. FIG. 1 shows that the energy consumption by both the control group and the IGF-1 supplied group was essentially the same. However, FIG. 2 indicates that, from the beginning of the infusion with IGF-1, the body weight of the IGF-1 treated group remained essentially stable, whilst that of the control group continued to fall. FIG. 3 shows that, during the time of IGF-1 infusion, the amount of nitrogen (in the form of urea) excreted by the control group was significantly greater than that excreated by the animals receiving IGF-1. This indicates that the rates of protein degradation was considerably higher in the control group than in the IGF-1 supplied group. FIG. 4 shows that, at the end of the experiment, the rats supplied with IGF-1 had a positive nitrogen balance (i.e they had accumulated protein); whereas, the control group had a negative nitrogen balance (i.e they had lost protein).

EXAMPLE 2

The following experiment was performed using cryptorchid crossbred lambs having an average weight of 16 kg and, within an age range of 3 to 5 months. The lambs were fasted for 48 hours and then placed in slings. Catheters were inserted into the external jugular veins to permit infusion. One group of five animals received an eight hour TPN nutrition infusion in which the protein load was 1.6 g/kg of body weight/day (i.e the maximum absorbable protein load for a sheep). The total caloric input was 50% of a sheep's normal daily requirement and of this 80% of the calories were in the form of carbohydrate (dextrose) and 20% in the form of lipids.

After three hours of this hypocaloric parenteral nutrition administration of authentic recombinant human IGF-1 was begun. The IGF-1 was infused at the rate of 50 microgram/kg/hour for five hours. The TPN was continued at the same rate as previously. Net protein loss was determined by $^{14}$C area turnover ($^{14}$C leucine having been incorporated into the TPN infusion).

Figure 5A:
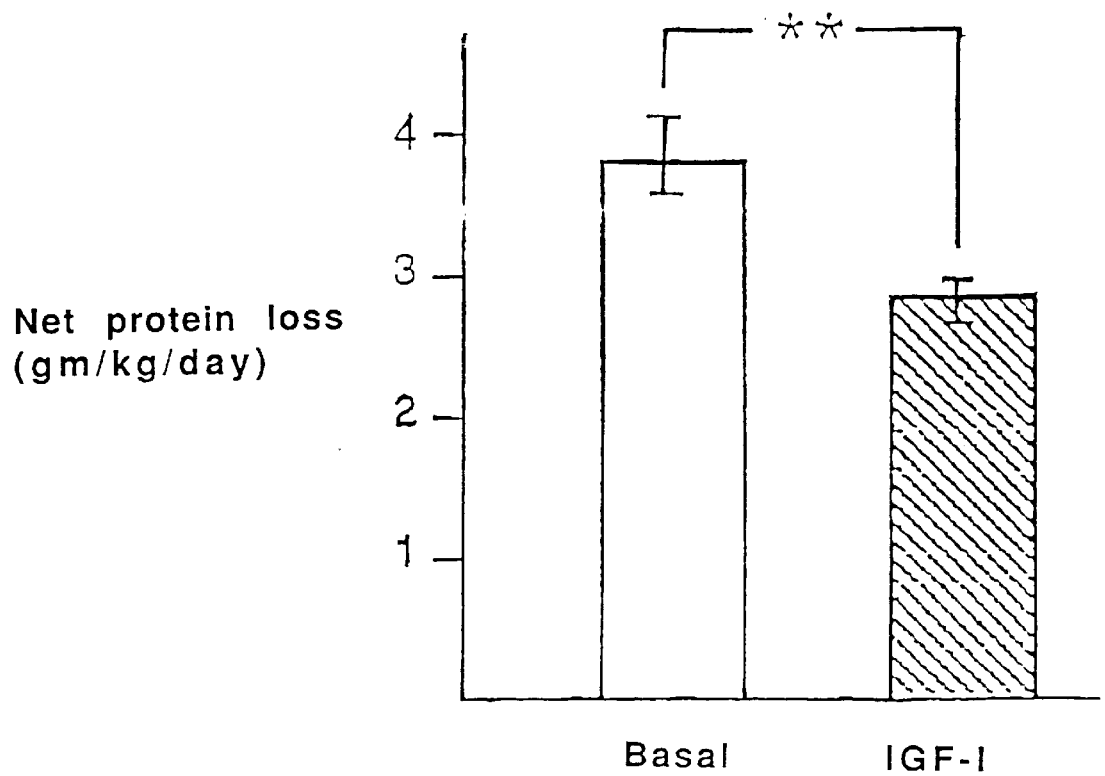
FIGS. 5a and 5b are graphs showing net protein loss.
Figure 5B:
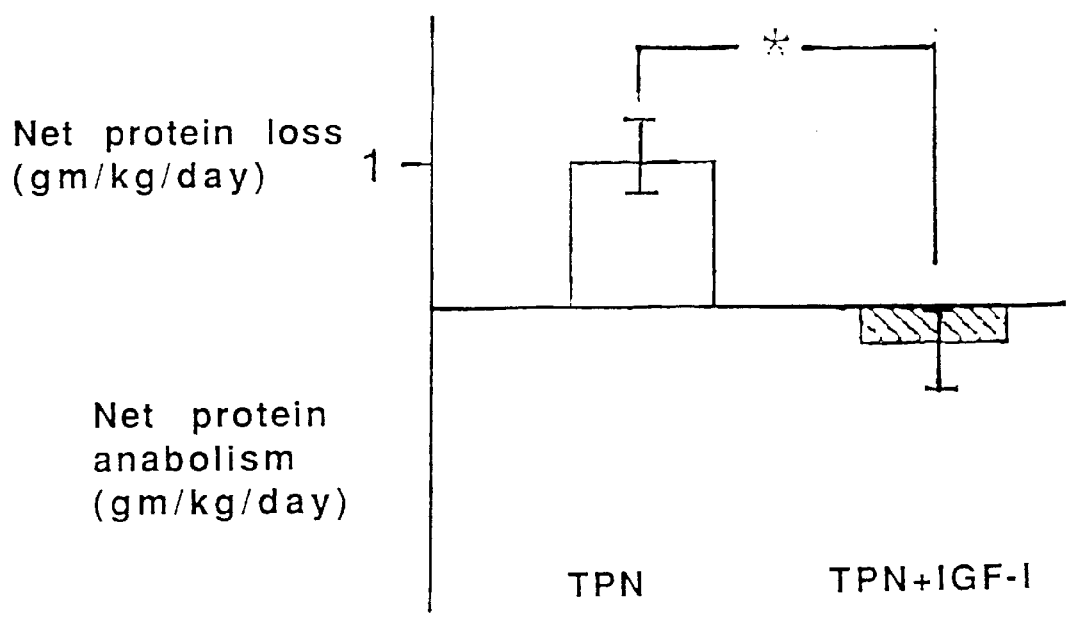

FIG. 5a shows, on the left-hand side, the basal rate of protein loss for fully-starved animals. On the right-hand side the graph shows that administration of IGF-1 alone in the rate indicated above slightly reduces the rate of protein loss (from about 3.8 to 2.8 g/kg/day) in starved lambs. FIG. 5b shows on the left-hand side that administration of TPN alone at the hypocaloric rate mentioned above reduces the rate of net protein loss to about 1g/kg/day. On the right-hand side is shown the effect of co-administration of hypocaloric TPN and IGF-1 at the rates indicated in the preceding two paragraphs.

Most surprisingly, instead of net protein loss, a net protein gain of around 0.25 gm/kg/day was observed. Thus, it has been determined that co-administration of IGF-1 with a diet providing only 50% of the normal caloric requirements (i.e the requirement for a stable condition in which protein is neither lost or gained) still leads to a significant net protein gain. Also surprising is that the effect of the combined administration of the hypocaloric TPN with the IGF-1 becomes apparent very rapidly, i.e during the five hour infusion period.

The fact that a net protein gain is achievable whilst providing only 50% of the normal caloric requirements is clinically important as it enables the total volume of the TPN and/or the protein load administered to be very substantially reduced. Volume considerations are especially important in the case of premature neonates, heart failure and renal disease. In the case of neonates in particular, TPN at conventional volume often leads to heart failure because of volume overload and the usual concomitant administration of diuretics. In the case of hepatic or renal disease it is advantageous to limit protein intake.

The fact that the effect of co-administration of IGF-1 and TPN is so rapid may be of life-saving importance in the case of critically ill patients.

EXAMPLE 3

To mimic the catabolism during a septic state, TNF can be administered in animal experiments. TNF is one of many substances, released from macrophages during endotoxin septicaemia, which replicates many of the clinical and metabolic features of sepsis, eg. fever, hypotension, anorexia, hyperglycemia and a negative nitrogen balance.

Four groups of lambs were fasted for 48 hours and thereafter subjected to constant iv. infusion of $^{15}$N-urea and $^6$H-glucose for 480 minutes. Two groups of lambs were simultaneously given TNF (1ug/kg/h) and two groups only saline.

During the last 300 minutes IGF-1 was infused (50ug/kg/h) in one each of the pretreated groups (TNF+saline) and saline was given to the remaining two groups of lambs (TNF+saline).

The infusion of rhIGF-1 caused a similar decrease in net protein catabolism (NPC) in lambs pretreated with TNF or saline (FIG. 6a,b), whereas no significant effect was observed in the control animals given saline instead of rhIGF-1.

Figure 6A:
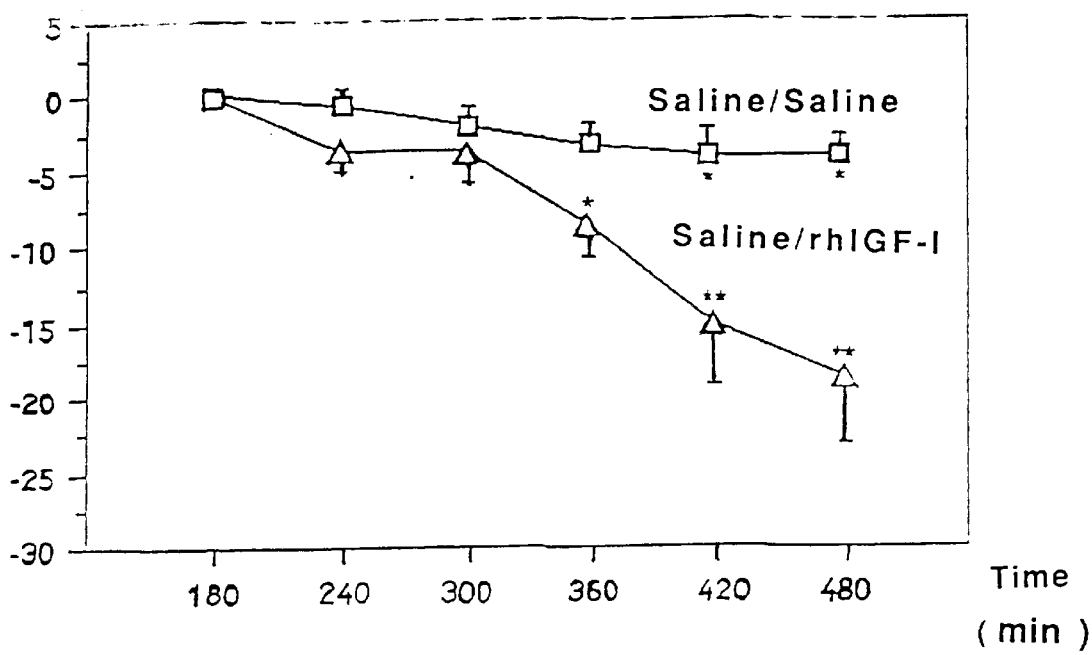
FIGS. 6a and 6b are graphs showing change of net protein loss due to rhIGF-1.
Figure 6B:
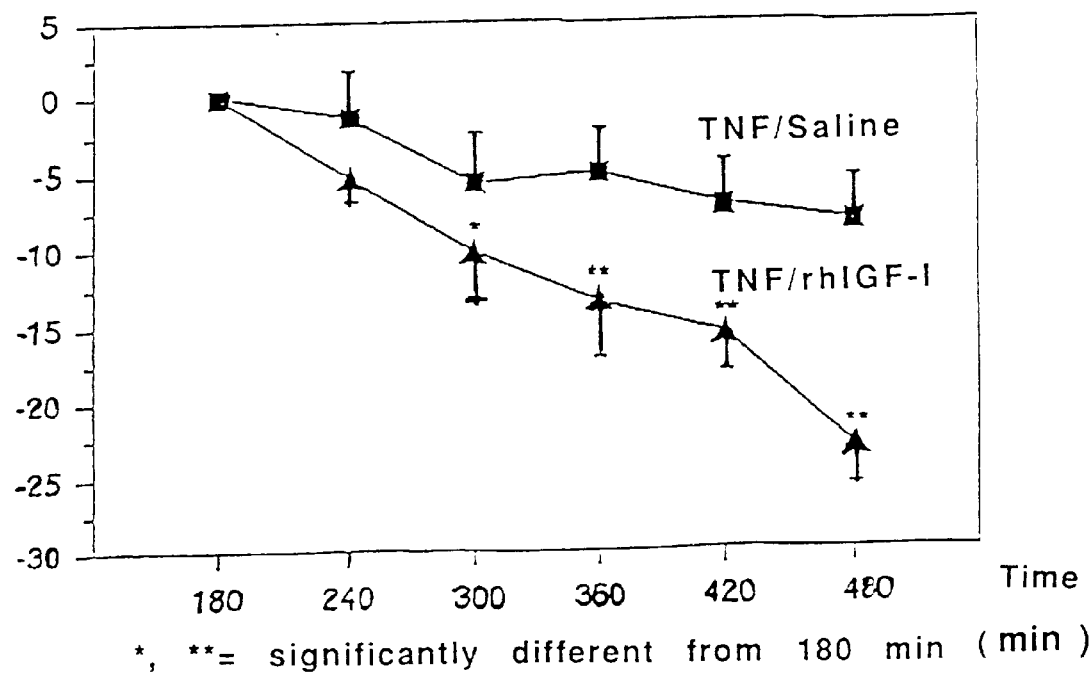

Furthermore, the effect was demonstrated to be equally rapid in both treatment groups, ie the effect of rhIGF-1 was significant already between 1 to 3 hours after the start of infusion (FIG. 6a, b).

EXAMPLE 4

The hormonal response to rhIGF-1 in the catabolic state was investigated in rats. In a rat model mimicking a trauma situation by fasting and a further food restriction (see table 1) we were able to demonstrate that rhIGF-1 significantly lowered circulating corticosterone (the active cortisone metabolite in the rat) (table 2).

TABLE 1

Anti-catabolic effect of IGF-1 in the food-restricted rat

| 100% Nutrition 5 days | Fast 2 days | 25% Nutrition 2 days | 50% Nutrition 3 days | 75% Nutrition 2 days |
|---|---|---|---|---|
| Treatments | IGF-1 | (s.c) | | No of animals |
| 1 | | 0 microgram/day | | 10 |
| 2 | | 200 microgram/day | | 10 |
| 3 | | 400 microgram/day | | 10 |
| 4 | | 1000 microgram/day | | 10 |

TABLE 2

Effects of s.c. IGF-1 injections on serum corticosterone(ng/ml)

| Treatment | Basal | Post-fast 50% | nutrition 75% |
|---|---|---|---|
| 1 (placebo) | 354 | 309 | 345 |
| 2 | 423 | 210 | 260 |
| 3 | 385 | 216 | 225 # |
| 4 | 490# | 183# | 88# |

# = p < 0.05 compared to placebo

This effect could be very important, since increased levels of cortisone (glucocorticosid) are the result of any stress/trauma situation. Cortisone itself affects intermediary metabolism, such as maintenance of glucose homeostasis, but is catabolic to muscle, where it decreases glucose uptake, decreases protein synthesis and increases the release of amino acids. (Basic & Clinical Endrocrinology, 1983 eds Greenspan & Korsham, p 266–273).

What is claimed is:

1. A method for the treatment of a catabolic state in a patient by administering to said patient in need thereof IGF-1 in conjunction with a hypocaloric diet wherein the amounts of IGF-1 and said hypocaloric diet are effective for said treatment of a catabolic state and wherein the amount of nutrient supplied by said hypocaloric diet utilized by said patient is up to 90% of the resting metabolic requirement of said patient.

2. The method of claim 1 wherein said IGF-1 and hypocaloric diet are administered simultaneously.

3. The method of claim 1 wherein said IGF-1 and hypocaloric diet are administered separately.

4. The method of claim 1 wherein said IGF-1 and hypocaloric diet are administered sequentially.

5. The method of claim 1 wherein the amount of said hypocaloric diet provides up to 60 kcal/kg of body weight for an adult per day.

6. The method of claim 1 wherein the amount of nutrient utilized by the patient is up to 70% of the resting metabolic requirement.

7. The method of claim 1 wherein the dose of said IGF-1 is 0.05 to 20 mg/kg/day.

8. The method of claim 1 wherein the dose of said IGF-1 is 0.02 to 2 mg/kg/day.

9. The method of claim 1 which comprises intravenous infusion of said IGF-1.

10. The method of claim 1 which comprises oral, intragastric or parenteral administration of said hypocaloric diet.

11. The method of claim 1 which comprises intravenous administration of said hypocaloric diet.

12. The method of claim 1 wherein said IGF-1 is administered orally or nasally or by subcutaneous or intramuscular injection.

\* \* \* \* \*